(12) United States Patent
Fujisaki

(10) Patent No.: US 9,770,198 B2
(45) Date of Patent: Sep. 26, 2017

(54) SENSOR AND FASTENER

(71) Applicant: NIHON KOHDEN CORPORATION, Tokyo (JP)

(72) Inventor: Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 243 days.

(21) Appl. No.: 14/482,213

(22) Filed: Sep. 10, 2014

(65) Prior Publication Data

US 2015/0099982 A1    Apr. 9, 2015

(30) Foreign Application Priority Data

Oct. 4, 2013   (JP) .................................. 2013-209470

(51) Int. Cl.
*A61B 5/1455*     (2006.01)
*A61B 5/00*       (2006.01)
(Continued)

(52) U.S. Cl.
CPC ...... *A61B 5/14551* (2013.01); *A61B 5/14552* (2013.01); *A61B 5/6803* (2013.01); *A61B 5/6814* (2013.01); *A61B 5/6831* (2013.01); *A61B 5/6843* (2013.01); *A61B 5/0082* (2013.01); *A61B 5/02108* (2013.01);
(Continued)

(58) Field of Classification Search
CPC .............. A61B 5/6803; A61B 5/14551; A61B 5/14552; A61B 5/14553; A61B 5/6814; A61B 5/6843; A61B 5/6831; A61B 5/02108; A61B 5/02438; A61B 2562/14;
(Continued)

(56) References Cited

U.S. PATENT DOCUMENTS 4,938,218 A    7/1990  Goodman et al.
5,099,842 A    3/1992  Mannheimer et al.
(Continued)

FOREIGN PATENT DOCUMENTS

CN    101461704 A    6/2009
JP    H04-501520 A   3/1992
(Continued)

OTHER PUBLICATIONS

The extended European Search Report for the related European Patent Application No. 14186102.1 dated Feb. 5, 2015.
(Continued)

*Primary Examiner* — Long V Le
*Assistant Examiner* — Angela M Hoffa
(74) *Attorney, Agent, or Firm* — Pearne & Gordon LLP

(57) ABSTRACT

A sensor which is adapted to attach to a head of a subject includes a first fastener that includes a first end portion and a second end portion and extends into an arc-shape, a first coupling portion that is disposed on an inner circumference side of the first fastener, a second fastener that has a first through hole and a second through hole, a second coupling portion that is disposed on a first side of the second fastener, and attachable to and detachable from the first coupling portion, a light emitter that is disposed on the first side of the second fastener, and opposed to the first through hole, and a light detector that is disposed on the first side of the second fastener, and opposed to the second through hole.

7 Claims, 4 Drawing Sheets

(51) Int. Cl.
*A61B 5/021* (2006.01)
*A61B 5/024* (2006.01)

(52) U.S. Cl.
CPC ....... *A61B 5/02433* (2013.01); *A61B 5/02438* (2013.01); *A61B 5/14553* (2013.01); *A61B 2560/0462* (2013.01); *A61B 2562/14* (2013.01); *A61B 2562/225* (2013.01)

(58) Field of Classification Search
CPC .............. A61B 5/0082; A61B 5/02433; A61B 2562/225; A61B 2560/0462
See application file for complete search history.

(56) References Cited

U.S. PATENT DOCUMENTS

| | | | |
|---|---|---|---|
| 5,109,849 A | 5/1992 | Goodman et al. | |
| 7,096,052 B2 * | 8/2006 | Mason | A61B 5/6814 600/310 |
| 7,164,938 B2 * | 1/2007 | Geddes | A61B 5/0059 600/324 |
| 7,190,986 B1 * | 3/2007 | Hannula | A61B 5/14552 600/310 |
| 8,483,790 B2 * | 7/2013 | Hannula | A61B 5/14552 600/310 |
| 8,852,095 B2 * | 10/2014 | Schlottau | A41D 1/002 2/171 |
| 9,138,181 B2 * | 9/2015 | Haisley | A61B 5/1455 |
| 2003/0109775 A1 | 6/2003 | O'Neil et al. | |
| 2004/0117891 A1 | 6/2004 | Hannula et al. | |
| 2004/0199063 A1 | 10/2004 | O'Neil et al. | |
| 2004/0221370 A1 | 11/2004 | Hannula et al. | |
| 2005/0070776 A1 | 3/2005 | Mannheimer et al. | |
| 2005/0283082 A1 * | 12/2005 | Geddes | A61B 5/0059 600/485 |
| 2006/0264726 A1 | 11/2006 | Mannheimer et al. | |
| 2006/0264727 A1 | 11/2006 | Mannheimer et al. | |
| 2006/0276700 A1 | 12/2006 | O'Neil et al. | |
| 2006/0281984 A1 | 12/2006 | Mannheimer et al. | |
| 2007/0219440 A1 * | 9/2007 | Hannula | A61B 5/14552 600/323 |
| 2008/0077023 A1 * | 3/2008 | Campbell | A61B 5/0205 600/502 |
| 2009/0105605 A1 | 4/2009 | Abreu | |
| 2009/0108205 A1 | 4/2009 | Duffy et al. | |
| 2011/0009723 A1 | 1/2011 | Mannheimer et al. | |
| 2012/0083673 A1 | 4/2012 | Al-Ali et al. | |
| 2013/0104288 A1 * | 5/2013 | Schlottau | A41D 1/002 2/209.13 |
| 2013/0158372 A1 * | 6/2013 | Haisley | A61B 5/1455 600/310 |
| 2013/0178725 A1 | 7/2013 | O'Neil et al. | |
| 2014/0135600 A1 | 5/2014 | O'Neil et al. | |
| 2014/0296669 A1 * | 10/2014 | Gertsch | A61B 5/6803 600/324 |

FOREIGN PATENT DOCUMENTS

| | | |
|---|---|---|
| JP | H05-048905 U | 6/1993 |
| JP | H05-076405 U | 10/1993 |
| JP | 2005-505360 A | 2/2005 |
| JP | 2007-524482 A | 8/2007 |

OTHER PUBLICATIONS

Office Action issued in Patent Application No. JP-2013-209470 dated Feb. 7, 2017.

* cited by examiner

SENSOR AND FASTENER

CROSS REFERENCE TO RELATED APPLICATION

This application is based on Japanese Patent Applications No. 2013-209470 filed on Oct. 4, 2013, the contents of which are incorporated herein by reference.

BACKGROUND

The presently disclosed subject matter relates to a sensor which is adapted to attach to the head of the subject to detect biological information, and also to a fastener which fastens the sensor to the head of the subject.

A sensor which is attached to the head of the subject to detect biological information is described in Patent Literature 1. Such a sensor is fastened to the head by a belt-like fastener in order to prevent dropping off from an attached portion (for example, see Patent Literature 2).

[Patent Literature 1] JP-T-2005-505360
[Patent Literature 2] JP-T-2007-524482

SUMMARY

The sensor disclosed in Patent Literature 1 includes a light emitter and a light detector. The light emitter and the light detector are placed on an attachment surface which is on the sensor body, and which is attached to the subject. The light emitter and the light detector are disposed so as to be projected from the attachment surface. When the sensor body is attached to the head, therefore, the tip ends of the light emitter and the light detector butt against the skin, and the subject feels discomfort. Moreover, the sensor body is pressed against the skin by a fastener such as that disclosed in Patent Literature 2. When the examination is performed for a long time, therefore, the subject feels pain in portions where the light emitter and the light detector butt against the skin.

Therefore, an object of the presently disclosed subject matter is to provide a technique for suppressing discomfort felt by the subject when a sensor is attached to the head.

In order to attain the object, a first aspect of the presently disclosed subject matter is a sensor which is attached to a head of a subject. The sensor includes a first fastener that includes a first end portion and a second end portion and extends into an arc-shape, a first coupling portion that is disposed on an inner circumference side of the first fastener, a second fastener that includes a first side, a second side, a first through hole, and a second through hole, a second coupling portion that is disposed on the first side of the second fastener, and attachable to and detachable from the first coupling portion, a light emitter that is disposed on the first side of the second fastener, and opposed to the first through hole, and a light detector that is disposed on the first side of the second fastener, and opposed to the second through hole. The first fastener has an elasticity which allows a gap between the first end portion and the second end portion to be expanded. The first coupling portion is placed at a position which is opposed to a forehead of the subject when the sensor is attached to the head of the subject. The first end portion and the second end portion are placed on a back of the head of the subject when the sensor is attached to the head of the subject. When the first coupling portion and the second coupling portion are coupled to each other, the light emitter and the light detector are disposed between the first fastener and the second fastener.

In order to attain the object, a second aspect of the presently disclosed subject matter is a second fastener which fastens a light emitter and a light detector to a first fastener that is attached to a head of a subject. The second fastener includes a first side, a second side that is opposite to the first side, and opposed to the subject, a first through hole that communicates between the first side and the second side, a second through hole that communicates between the first side and the second side, and a second coupling portion that is disposed on the first side, and attachable to and detachable from a first coupling portion of the first fastener. When the second coupling portion is coupled to the first coupling portion, the light emitter and the light detector are able to be disposed between the second fastener and the first fastener.

According to the configuration, the first and second end portions of the first fastener which extends in an arc-shape are separated from each other, and the first fastener has the elasticity which allows the gap between the end portions to be expanded. The light emitter and the light detector are held between the first and second fasteners by the coupling between the first and second coupling portions. Therefore, the sensor can be easily attached by one operation from the front side of the forehead of the subject. Even during sleeping of the subject, for example, the sensor can be attached to the subject without requiring a work of raising the head of the subject. Therefore, the workability is improved for the medical person, and troublesome for the subject in attachment of the sensor can be suppressed.

Since the light emitter and the light detector are held between the first and second fasteners, it is not necessary for the first fastener to generate a force for pressing the light emitter and the light detector against the forehead of the subject to hold them. It is sufficient for the first fastener to generate a force of a degree at which the second fastener is caused to be in close contact with the forehead of the subject to such an extent that the measurement using the light emitter and the light detector is enabled. Therefore, the second fastener is not pressed against the forehead more than necessary, and discomfort felt by the subject can be suppressed.

At this time, the light emitter and the light detector are disposed between the first and second fasteners, and do not butt against the forehead of the subject. The second fastener which is larger in contact area than the light emitter and the light detector butts against the forehead, whereby the pressing force is dispersed, and discomfort felt by the subject can be suppressed.

A configuration may be employed where the second side which is opposite to the first side has a first portion having a first elasticity, and a second portion having a second elasticity which is lower than the first elasticity, and the second portion extends through an area between the first through hole and the second through hole.

According to the configuration, when the sensor is attached to the forehead of the subject, the first portion is deformed in accordance with the shape of the forehead. Therefore, the adhesiveness of the second fastener to the forehead is enhanced, and a sense of oppression felt by the subject can be reduced. At this time, the amount of deformation of the second portion having the elasticity which is lower than the first elasticity is smaller than that of the first portion, and the second portion functions as a division wall between the first and second through holes. Therefore, a situation where a light beam which is emitted from the light emitter, and which passes through the first through hole enters toward the second through hole to be detected by the light detector, without being reflected from the forehead of the subject can be prevented from occurring. Namely, biological information of the subject can be correctly acquired while suppressing discomfort which is due to the sense of oppression, and which is felt by the subject.

A configuration may be employed where the first side of the second fastener includes a first recess and a second recess. In this case, the light emitter is placed in the first recess, and the light detector is placed in the second recess.

According to the configuration, the light emitter and the light detector are surely positioned, so that the holdability is enhanced, and the thickness of the second fastener can be reduced. Therefore, an uncomfortable sensation due to the contacting of the second fastener in attachment of the sensor can be reduced, and discomfort felt by the subject can be suppressed.

A configuration may be employed where the first fastener includes a mechanism to adjust a length in a longitudinal direction of the first fastener.

According to the configuration, the length in the longitudinal direction of the first fastener can be adjusted in accordance with the size of the head of the subject. Therefore, an uncomfortable sensation due to the attachment of the first fastener can be reduced according the subject, and hence discomfort felt by the subject during the attachment of the sensor can be suppressed.

A configuration may be employed where the first fastener includes: a first cable holder which is disposed on a side of the first end portion with respect to a center portion in the longitudinal direction; and a second cable holder which is disposed on a side of the second end portion with respect to the center portion. In this case, the first cable holder and the second cable holder are configured so as to be able to hold cables connected to the light emitter and the light detector, respectively.

According to the configuration, the cables extending from the light emitter and light detector which are attached to the forehead are prevented from swinging in front of the eyes. Therefore, discomfort felt by the subject can be suppressed, and noise contamination in signals transmitted through the cables is prevented from occurring. According to the taste of the subject, or examination conditions, at least one of the first and second cable holders can be used. Therefore, the cables can be held in a mode where the subject hardly feels an uncomfortable sensation.

A configuration may be employed where the first coupling portion is a loop side of a hook and loop fastener, and the second coupling portion is a hook side of the hook and loop fastener.

The first coupling portion is disposed on the side of the inner circumference of the first fastener. Therefore, the first coupling portion which is disposed in a place other than the place where the second coupling portion couples to the first coupling portion butts against the forehead of the subject. However, the loop side of a hook and loop fastener has soft texture. Therefore, discomfort felt by the subject can be suppressed.

DETAILED DESCRIPTION OF EMBODIMENTS

Figure 1:
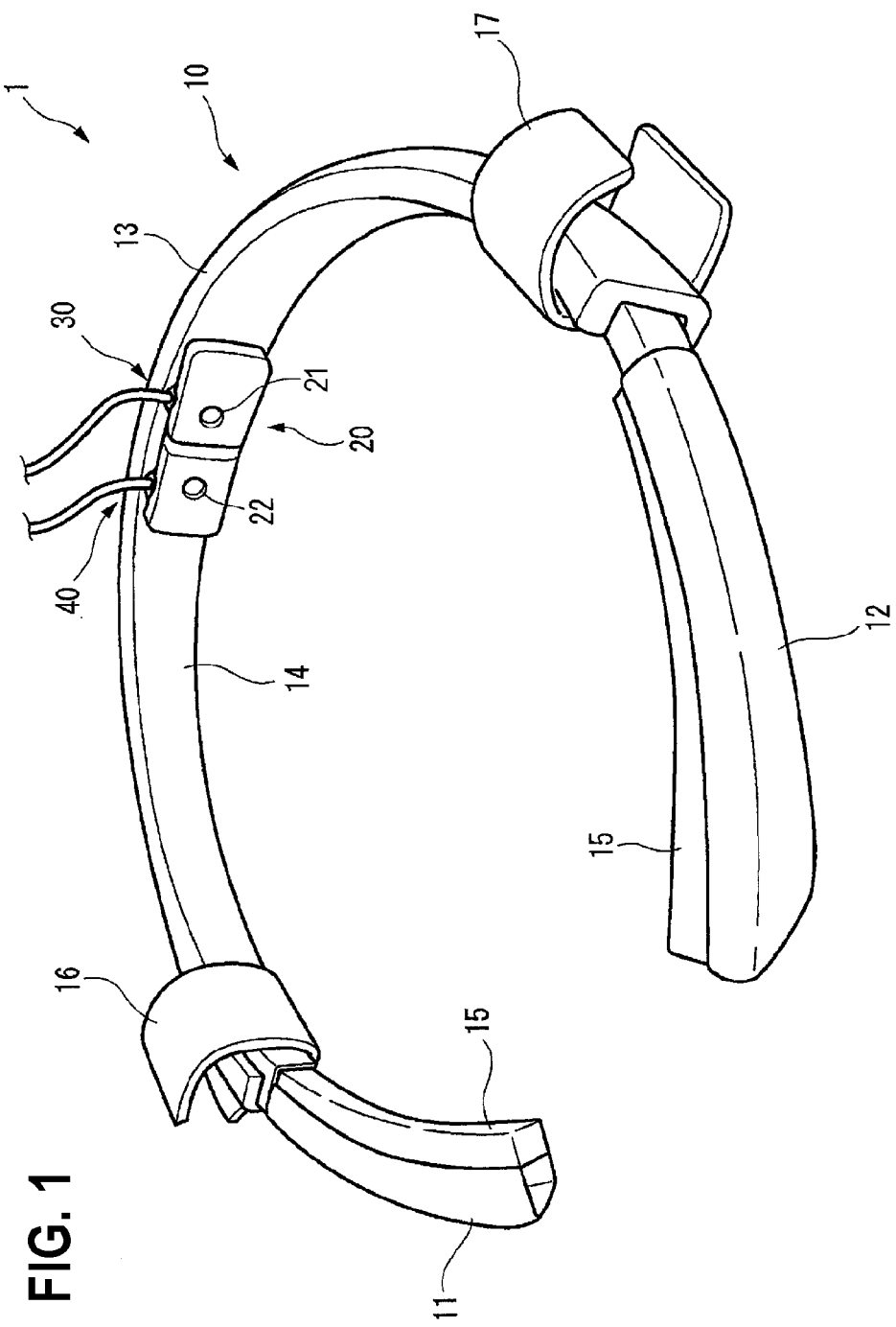
FIG. 1 is a perspective view illustrating a sensor of an embodiment of the presently disclosed subject matter.

Hereinafter, an embodiment of the presently disclosed subject matter will be described in detail with reference to the accompanying drawings. In the drawings which will be used in the following description, the scale is adequately changed in order to draw components in a recognizable size.

FIG. 1 is a perspective view illustrating a sensor 1 of an embodiment of the presently disclosed subject matter. The sensor 1 which is to be attached to the head of the subject can include a first fastener 10, a second fastener 20, a light emitter 30, and a light detector 40.

The first fastener 10 can include a first end portion 11, a second end portion 12, and a body portion 13. The first end portion 11 is connected to a left end part of the body portion 13. The second end portion 12 is connected to a right end part of the body portion 13.

The first fastener 10 extends in an arcuate shape as a whole, and the first end portion 11 and the second end portion 12 are separated from each other. The first fastener 10 has an elasticity which allows the gap between the first and second end portions 11, 12 to be expandingly opened.

A first coupling portion 14 is disposed on the side of the inner circumference of the body portion 13. For example, the first coupling portion 14 is the loop side of a hook and loop fastener. Cushion members 15 are disposed on the inner circumferential sides of the first and second end portions 11, 12, respectively. An example of the material of the cushion members 15 is a low elasticity sponge.

The second fastener 20 has a first side which is opposed to the inner circumferential side of the first fastener 10, and a second side which is opposite to the first side. The second fastener 20 has first and second through holes 21, 22 communicating between the first side and the second side.

Figure 2A:
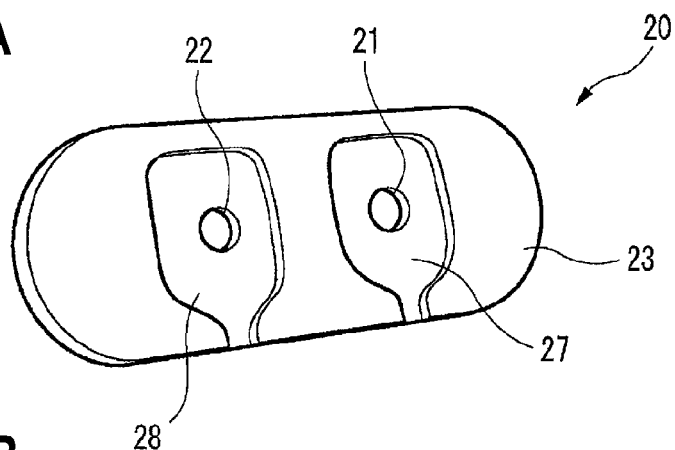
FIGS. 2A to 2C illustrate the configuration of a first side of a second fastener of the sensor of FIG. 1.

FIG. 2A is a perspective view enlargedly illustrating the first side of the second fastener 20. A second coupling portion 23 is disposed on the first side. For example, the second coupling portion 23 is the hook side of the hook and loop fastener, and attachable to and detachable from the first coupling portion 14 of the first fastener 10.

Figure 2B:
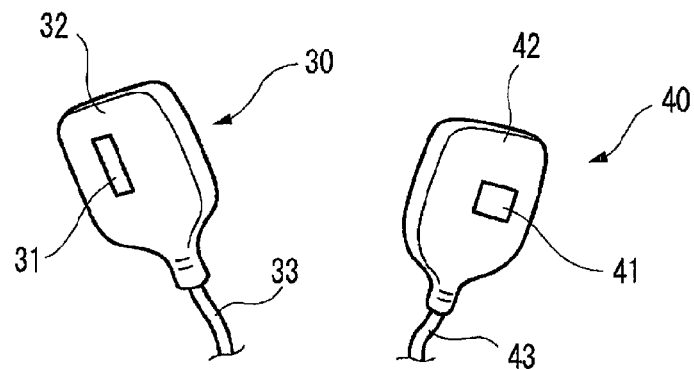

FIG. 2B is a perspective view illustrating the light emitter 30 and the light detector 40. The light emitter 30 can include a light emitting portion 31, an attaching portion 32, and a signal line 33. The light detector 40 can include a light detecting portion 41, an attaching portion 42, and a signal line 43.

The light emitting portion 31 emits light having a predetermined wavelength in accordance with a control signal which is input from a controller (not shown) through the signal line 33. The attaching portion 32 is disposed so as to surround the light emitting portion 31, and attachable to and detachable from the second coupling portion 23 of the second fastener 20. For example, the attaching portion 32 may be configured by a rubber material, a towel cloth, a pile fabric, or the loop side of the hook and loop fastener.

The light detecting portion 41 outputs a signal corresponding to the intensity of received light, through the signal line 43. The attaching portion 42 is disposed so as to surround the light detecting portion 41, and attachable to and detachable from the second coupling portion 23 of the second fastener 20. For example, the attaching portion 42 may be configured by a rubber material, a towel cloth, a pile fabric, or the loop side of the hook and loop fastener.

Figure 2C:
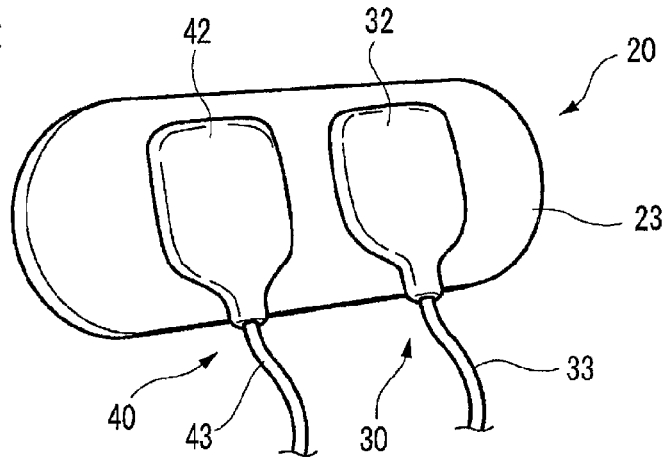

As shown in FIG. 2C, the light emitter 30 and the light detector 40 are placed on the first side of the second fastener 20. Specifically, they are placed so that the light emitting portion 31 of the light emitter 30 is opposed to the first through hole 21, and the light detecting portion 41 of the light detector 40 is opposed to the second through hole 22.

As shown in FIG. 1, the second fastener 20 is attached to the inner circumferential side of the body portion 13 of the first fastener 10. At this time, the first coupling portion 14 and the second coupling portion 23 are coupled to each other, and the light emitter 30 and the light detector 40 are disposed between the first fastener 10 and the second fastener 20. The place where the second fastener 20 is attached may be arbitrarily determined according to the subject, as far as the place is within the range where the first coupling portion 14 is disposed.

Figure 3A:
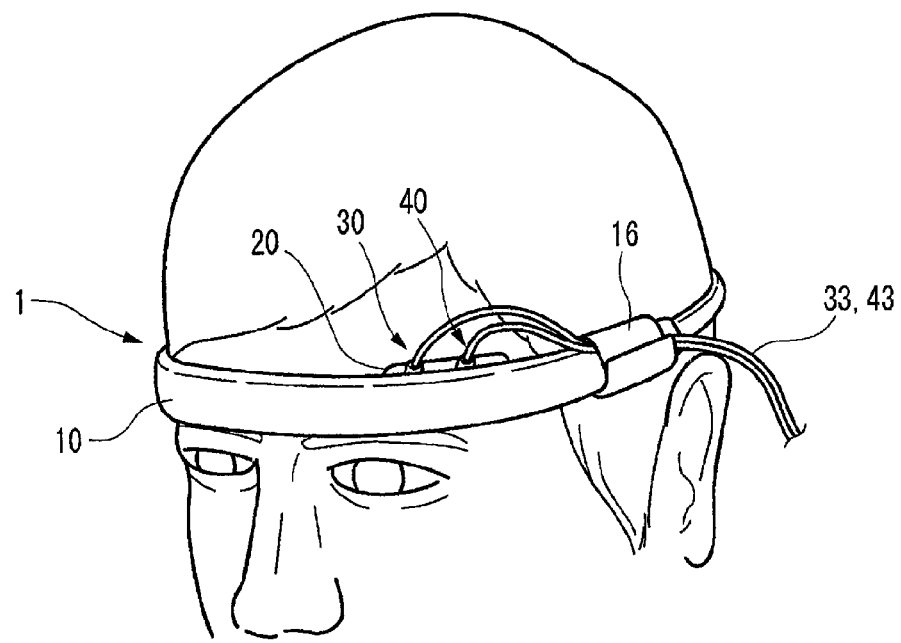
FIGS. 3A and 3B illustrate a state where the sensor of FIG. 1 is attached to the head of the subject.
Figure 3B:
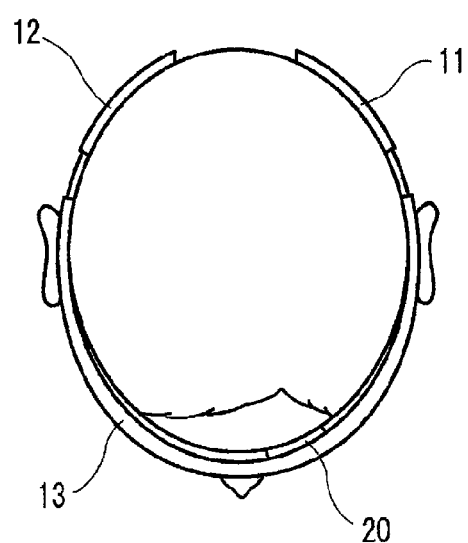

FIG. 3A is a perspective view illustrating a state where the sensor having the above-described configuration is attached to the head of the subject, and FIG. 3B illustrates the state as viewed from above the head. In the attachment of the sensor 1, the first coupling portion 14 of the first fastener 10 is placed at a position that is opposed to the forehead of the subject. In the attachment of the sensor 1, moreover, the first end portion 11 and second end portion 12 of the first fastener 10 are placed on the back of the head of the subject.

For example, the light emitter 30 and the light detector 40 are used as a probe of a pulse oximeter. In this case, the light emitter is configured so as to emit a red light and an infrared light. The forehead of the subject is irradiated with the red and infrared light emitted from the light emitting portion 31 of the light emitter 30 through the first through hole 21 of the second fastener 20. The red and infrared light which are reflected from the forehead are detected by the light detecting portion 41 of the light detector 40 through the second through hole 22 of the second fastener 20. In hemoglobin in blood, absorbance of a red light and absorbance of an infrared light are different depending on presence or absence of oxygenation. When the intensities of the red light and the infrared light detected by the light detector 41 are analyzed, therefore, it is possible to measure the arterial oxygen saturation (SpO2). When the pulse wave component due to the pulsation of the heart is detected, it is possible to measure the pulse rate.

In the thus configured sensor 1, the first end portion 11 and second end portion of the first fastener 10 which arcuately extends are separated from each other, and the first fastener has an elasticity which allows the gap between the end portions to be expandingly opened. The light emitter 30 and the light detector 40 are held between the first and second fasteners 10, 20 by the coupling between the first and second coupling portions 14, 23. Therefore, the sensor 1 can be easily attached by one operation from the front side of the forehead of the subject. Even during sleeping of the subject, for example, the sensor 1 can be attached to the subject without requiring a work of raising the head of the subject. Therefore, the workability is improved for the medical person, and troublesome for the subject in the attachment of the sensor 1 can be suppressed.

Since the light emitter 30 and the light detector 40 are held between the first and second fasteners 10, 20, the first fastener 10 is not required to generate a force for pressing the light emitter 30 and the light detector 40 against the forehead of the subject to hold them. It is sufficient for the first fastener 10 to generate a force of a degree at which the second fastener 20 is caused to be in close contact with the forehead of the subject to such an extent that the measurement using the light emitter 30 and the light detector 40 is enabled. In the attachment of the sensor 1, the configuration shown in FIG. 3B where the first end portion 11 and the second end portion go around to the back of the head of the subject cooperates with the elasticity of the first fastener 10 itself to enable generation of such a force. Therefore, the second fastener 20 is not pressed against the forehead more than necessary, and discomfort felt by the subject can be suppressed.

At this time, the light emitter 30 and the light detector 40 are disposed between the first and second fasteners 10, 20, and do not butt against the forehead of the subject. The second fastener 20 which is larger in contact area than the light emitter 30 and the light detector 40 butts against the forehead, whereby the pressing force is dispersed, and discomfort felt by the subject can be suppressed.

Figure 4:
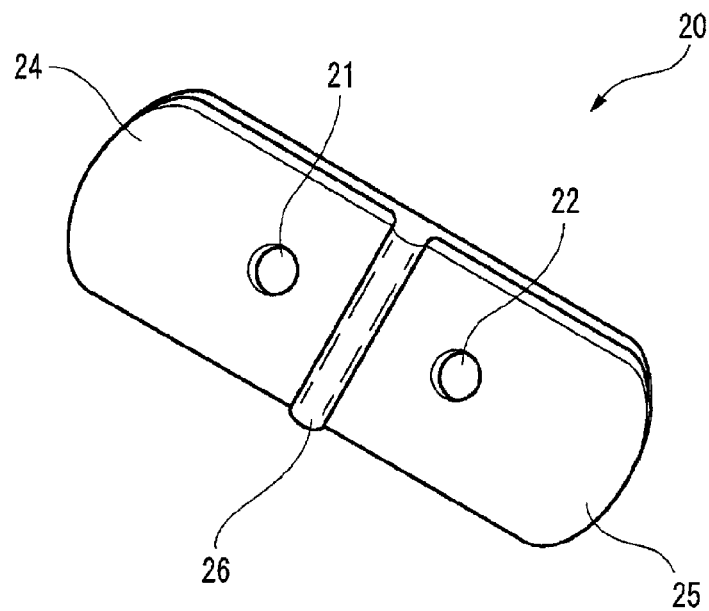
FIG. 4 illustrates the configuration of a second side of the second fastener of the sensor of FIG. 1.

As shown in FIG. 4, the second side of the second fastener 20 has a left contacting portion 24, a right contacting portion 25, and a center contacting portion 26. The left and right contacting portions 24, 25 (an example of the first portion) are formed by, for example, a sponge, and have an elasticity. The center contacting portion 26 (an example of the second portion) is formed by, for example, a low elastic sponge, and has an elasticity which is lower than that of the left and right contacting portions 24, 25.

The first through hole 21 is opened in the left contacting portion 24, and the second through hole 22 is opened in the right contacting portion 25. The center contacting portion 26 extends so as to traverse the area between the first and second through holes 21, 22.

According to the configuration, when the sensor 1 is attached to the forehead of the subject, the left and right contacting portions 24, 25 are deformed in accordance with the shape of the forehead. Therefore, the adhesiveness of the second fastener 20 to the forehead is enhanced, and a sense of oppression felt by the subject can be reduced. At this time, the amount of deformation of the center contacting portion 26 having the elasticity which is lower than the left and right contacting portions 24, 25 is smaller than the amounts of deformation of the left and right contacting portions 24, 25, and the center contacting portion functions as a division wall between the first and second through holes 21, 22. Therefore, a situation where a light emitted from the light emitter 30 passes through the first through hole 21 enters toward the second through hole 22 to be detected by the light detector 40, without being reflected from the forehead of the subject can be prevented from occurring. Namely, biological information of the subject can be correctly acquired while suppressing discomfort which is due to the sense of oppression, and which is felt by the subject.

As shown in FIG. 2A, a first recess 27 and a second recess 28 are formed respectively in parts of the second coupling portion 23 which is disposed on the first side of the second fastener 20. The first through hole 21 is opened in the bottom of the first recess 27, and the second through hole 22 is opened in the bottom of the second recess 28. The shapes of the first and second recesses 27, 28 correspond to the attaching portion 32 of the light emitter 30 and the attaching portion 42 of the light detector 40, respectively. In the state shown in FIG. 2C where the light emitter 30 and the light detector 40 are attached, the attaching portion 32 is placed in the first recess 27, and the attaching portion 42 is placed in the second recess 28.

The bottoms of the first and second recesses 27, 28 may be configured in an adequate mode as far as the attaching portion 32 of the light emitter 30 and the attaching portion 42 of the light detector 40 can be detachably coupled to the recesses. Each of the bottoms may be configured as the loop side of a hook and loop fastener in a similar manner as the second coupling portion 23, or an adhesive tape may be disposed.

According to the configuration, the light emitter 30 and the light detector 40 are surely positioned, so that the holdability is enhanced, and the thickness of the second fastener 20 can be reduced. Therefore, an uncomfortable sensation due to the contacting of the second fastener 20 in the attachment of the sensor 1 can be reduced, and discomfort felt by the subject can be suppressed.

Figure 5:
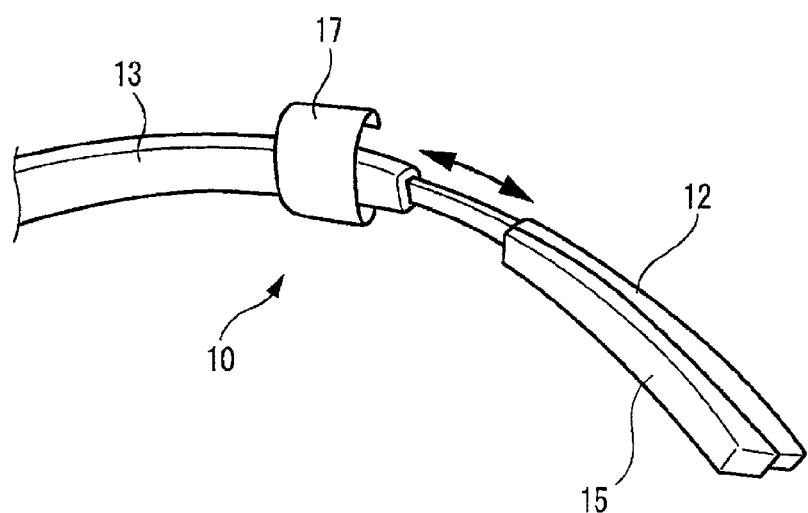
FIG. 5 is a perspective view illustrating the configuration of an end portion of a first fastener of the sensor of FIG. 1.

As shown in FIG. 5, the second end portion 12 of the first fastener 10 is supported in a manner that it is slidable relative to the body portion 13. Although not illustrated, also the first end portion 11 is similarly configured. Therefore, the length in the longitudinal direction of the first fastener 10 can be adjusted. In the attachment of the sensor 1, the sliding distance can be adjusted so that the first end portion 11 and the second end portion 12 are placed on the back of the head of the subject.

According to the configuration, the length in the longitudinal direction of the first fastener 10 can be adjusted in accordance with the size of the head of the subject. Therefore, an uncomfortable sensation due to the attachment of the first fastener 10 can be reduced according to the subject, and hence discomfort felt by the subject during the attachment of the sensor 1 can be suppressed.

As shown in FIG. 1, the first fastener 10 can include a first cable holder 16 and a second cable holder 17. The first cable holder 16 is disposed on the side of the first end portion 11 with respect to the center portion in the longitudinal direction of the first fastener 10. The second cable holder 17 is disposed on the side of the second end portion 12 with respect to the center portion in the longitudinal direction of the first fastener 10.

The first cable holder 16 and the second cable holder 17 are configured so as to be able to hold signal lines 33, 43 (examples of the cables) connected to the light emitter 30 and the light detector 40, respectively. As shown in FIG. 3A, one of the first cable holder 16 and the second cable holder 17 may hold both the signal lines 33, 43, or the first cable holder 16 and the second cable holder 17 may hold the signal lines 33, 43, respectively (the reverse is also possible). In the embodiment, the first cable holder 16 and the second cable holder 17 are configured by a pair of belts which are attachable to and detachable from each other by means of a hook and loop fastener. Another holding structure may be employed as far as the signal lines 33, 43 can be held.

According to the configuration, the signal lines 33, 43 extending from the light emitter 30 and light detector 40 which are attached to the forehead are prevented from swinging in front of the eyes. Therefore, discomfort felt by the subject can be suppressed, and noise contamination in signals transmitted through the signal lines 33, 43 is prevented from occurring. According to the taste of the subject, or examination conditions, at least one of the first and second cable holders 16, 17 can be used. Therefore, the cables can be held in a mode where the subject hardly feels an uncomfortable sensation.

The embodiment has been described in order to facilitate understanding of the presently disclosed subject matter, and is not intended to limit the presently disclosed subject matter. It is a matter of course that the presently disclosed subject matter may be changed or improved without departing the spirit thereof, and includes equivalent embodiments.

In the embodiment, the loop side of a hook and loop fastener is used as the first coupling portion 14 of the first fastener 10, and the hook side of the hook and loop fastener is used as the second coupling portion 23 of the second fastener 20.

The first coupling portion 14 is disposed on the side of the inner circumference of the first fastener 10. Therefore, the first coupling portion which is disposed in a place other than the place where the second coupling portion 23 couples to the first coupling portion butts against the forehead of the subject. However, the loop side of a hook and loop fastener has soft texture. Therefore, discomfort felt by the subject can be suppressed.

As far as the first and second coupling portions 14, 23 are attachable to and detachable from each other, the portions may have a configuration other than a hook and loop fastener. For example, tape members in each of which the surface has a silicone adhesive layer having a re-adhesion property may be used as the first and second coupling portions 14, 23, respectively.

The mechanism which enables the length in the longitudinal direction of the first fastener 10 to be adjusted is not limited to the sliding mechanism for the first and second end portions 11, 12. As far as the length in the longitudinal direction of the first fastener 10 can be adjusted, an adequate mechanism may be employed in at least one of the first and second end portions 11, 12 and the body portion 13.

1: sensor
10: first fastener
11: first end portion
12: second end portion
14: first coupling portion
16: first cable holder
17: second cable holder
20: second fastener
21: first through hole
22: second through hole
23: second coupling portion
24: left contacting portion
25: right contacting portion
26: center contacting portion
27: first recess
28: second recess
30: light emitter
40: light detector

What is claimed is:
1. A sensor which is adapted to attach to a head of a subject comprising:
 a first fastener that includes a first end portion and a second end portion and extends into an arc-shape;
 a first coupling portion that is disposed on an inner circumference side of the first fastener;
 a second fastener that includes a first side, a second side, a first contacting portion with a first through hole, a second contacting portion with a second through hole, and a central portion, wherein the first contacting portion and the second contacting portion have a first elasticity, the first contacting portion and the second contacting portion are connected by the central portion, and the central portion has a second elasticity which is lower than the first elasticity;
 a second coupling portion that is disposed on the first side of the second fastener, and attachable to and detachable from the first coupling portion;
 a light emitter that is disposed on the first side of the second fastener, and opposed to the first through hole; and a light detector that is disposed on the first side of the second fastener, and opposed to the second through hole, wherein the light emitter and the light detector are directly in contact with the first coupling portion, wherein the first fastener has an elasticity which allows a gap between the first end portion and the second end portion to be expanded, the first coupling portion is placed at a position which is opposed to a forehead of the subject when the sensor is attached to the head of the subject, the first end portion and the second end portion are placed on a back of the head of the subject when the sensor is attached to the head of the subject, and, when the first coupling portion and the second coupling portion are coupled to each other, the light emitter and the light detector are disposed between the first fastener and the second fastener.

2. The sensor according to claim 1, wherein the first side of the second fastener includes a first recess and a second recess, the light emitter is placed in the first recess, and the light detector is placed in the second recess.

3. The sensor according to claim 1, wherein the first fastener includes a mechanism to adjust a length in a longitudinal direction of the first fastener.

4. The sensor according to claim 1, wherein the first fastener includes:

a first cable holder which is disposed on a side of the first end portion of the first fastener with respect to a center portion of the first fastener in the longitudinal direction; and a second cable holder which is disposed on a side of the second end portion of the first fastener with respect to the center portion of the first fastener, and the first cable holder and the second cable holder are configured so as to be able to hold cables connected to the light emitter and the light detector, respectively.

5. The sensor according to claim 1, wherein the first coupling portion is a loop side of a hook and loop fastener, and the second coupling portion is a hook side of the hook and loop fastener.

6. A second fastener which fastens a light emitter and a light detector to a first fastener that is adapted to attach to a head of a subject, comprising:

a first side;

a second side that is opposite to the first side, and opposed to the subject;

a first contacting portion with a first through hole that communicates between the first side and the second side;

a second contacting portion with a second through hole that communicates between the first side and the second side;

a central portion, wherein the first contacting portion and the second contacting portion have a first elasticity, the first contacting portion and the second contacting portion are connected by the central portion, and the central portion has a second elasticity which is lower than the first elasticity; and a second coupling portion that is disposed on the first side, and attachable to and detachable from a first coupling portion of the first fastener, and, when the second coupling portion is coupled to the first coupling portion, the light emitter and the light detector are able to be disposed between the second fastener and the first fastener wherein the light emitter and the light detector are directly in contact with the first coupling portion.

7. The second fastener according to claim 6, wherein the second fastener further includes:

a first recess that is formed in the first side of the second fastener, and able to hold the light emitter; and a second recess that is formed in the first side of the second fastener, and able to hold the light detector.

* * * * *